(12) United States Patent
Bokor et al.

(10) Patent No.: US 6,555,828 B1
(45) Date of Patent: Apr. 29, 2003

(54) METHOD AND APPARATUS FOR INSPECTING REFLECTION MASKS FOR DEFECTS

(75) Inventors: Jeffrey Bokor, Oakland, CA (US); Yun Lin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/193,198

(22) Filed: Nov. 17, 1998

(51) Int. Cl.[7] .............................................. G01B 15/06
(52) U.S. Cl. ............................. 250/492.2; 250/492.1; 250/492.3
(58) Field of Search .......................... 250/492.2, 492.3, 250/492.1, 306; 430/5, 311

(56) References Cited

U.S. PATENT DOCUMENTS

| 4,481,531 A | * | 11/1984 | Warde et al. ................. 358/60 |
| 5,691,541 A | * | 11/1997 | Ceglio et al. ............ 250/492.1 |
| 5,715,052 A | * | 2/1998 | Fujino et al. .......... 250/559.41 |
| 6,002,740 A | * | 12/1999 | Cerrina et al. ................ 378/35 |
| 6,042,995 A | * | 3/2000 | White ........................ 430/311 |

OTHER PUBLICATIONS

Lin, Yun et al. "Minimum critical defects in extreme–ultraviolet lithography masks" *J. Vac. Sci. Technol.* B15(6), pp. 2467–2470 (1997).

* cited by examiner

*Primary Examiner*—John R. Lee
*Assistant Examiner*—Anthony Quash
(74) *Attorney, Agent, or Firm*—Fliesler Dubb Meyer & Lovejoy LLP

(57) ABSTRACT

An at-wavelength system for extreme ultraviolet lithography mask blank defect detection is provided. When a focused beam of wavelength 13 nm is incident on a defective region of a mask blank, three possible phenomena can occur. The defect will induce an intensity reduction in the specularly reflected beam, scatter incoming photons into an off-specular direction, and change the amplitude and phase of the electric field at the surface which can be monitored through the change in the photoemission current. The magnitude of these changes will depend on the incident beam size, and the nature, extent and size of the defect. Inspection of the mask blank is performed by scanning the mask blank with 13 nm light focused to a spot a few μm in diameter, while measuring the reflected beam intensity (bright field detection), the scattered beam intensity (dark-field detection) and/or the change in the photoemission current.

12 Claims, 6 Drawing Sheets

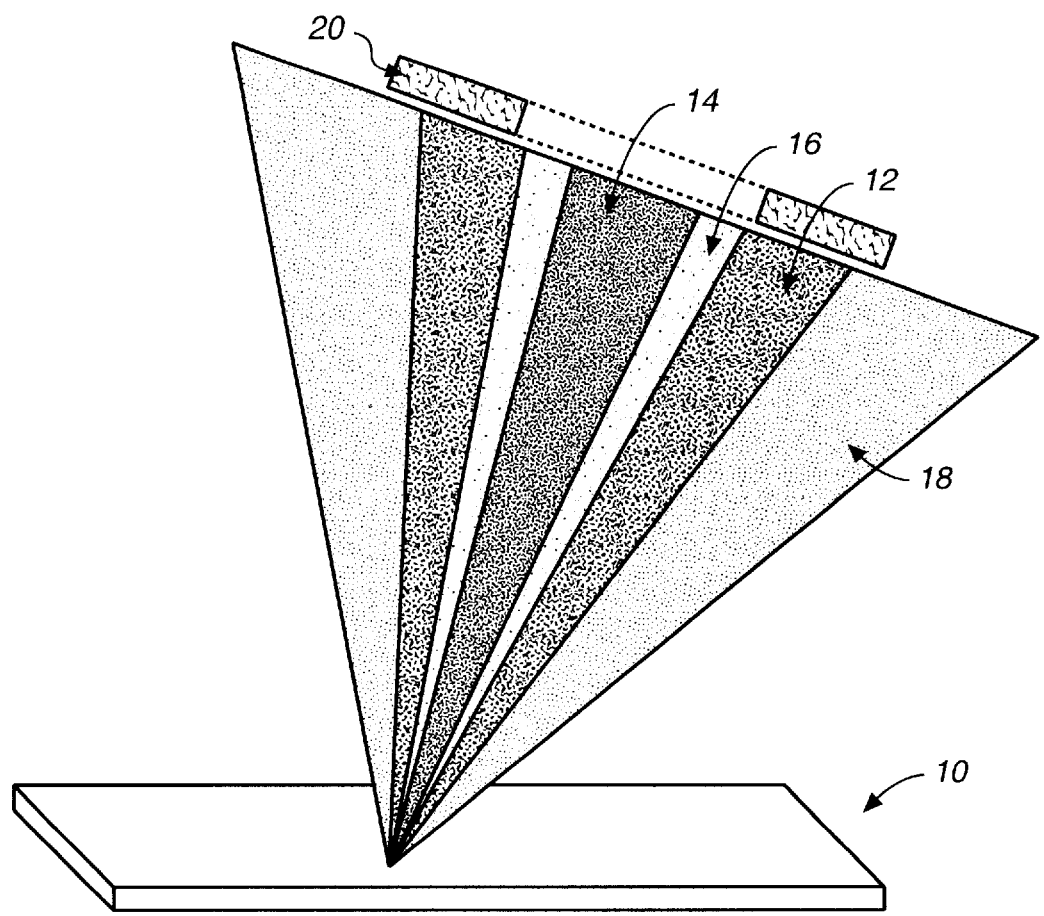
FIG._1
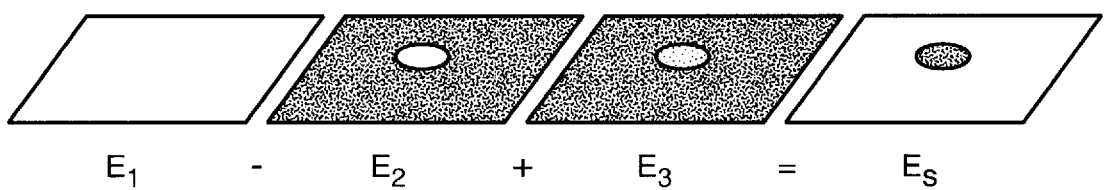
FIG._2

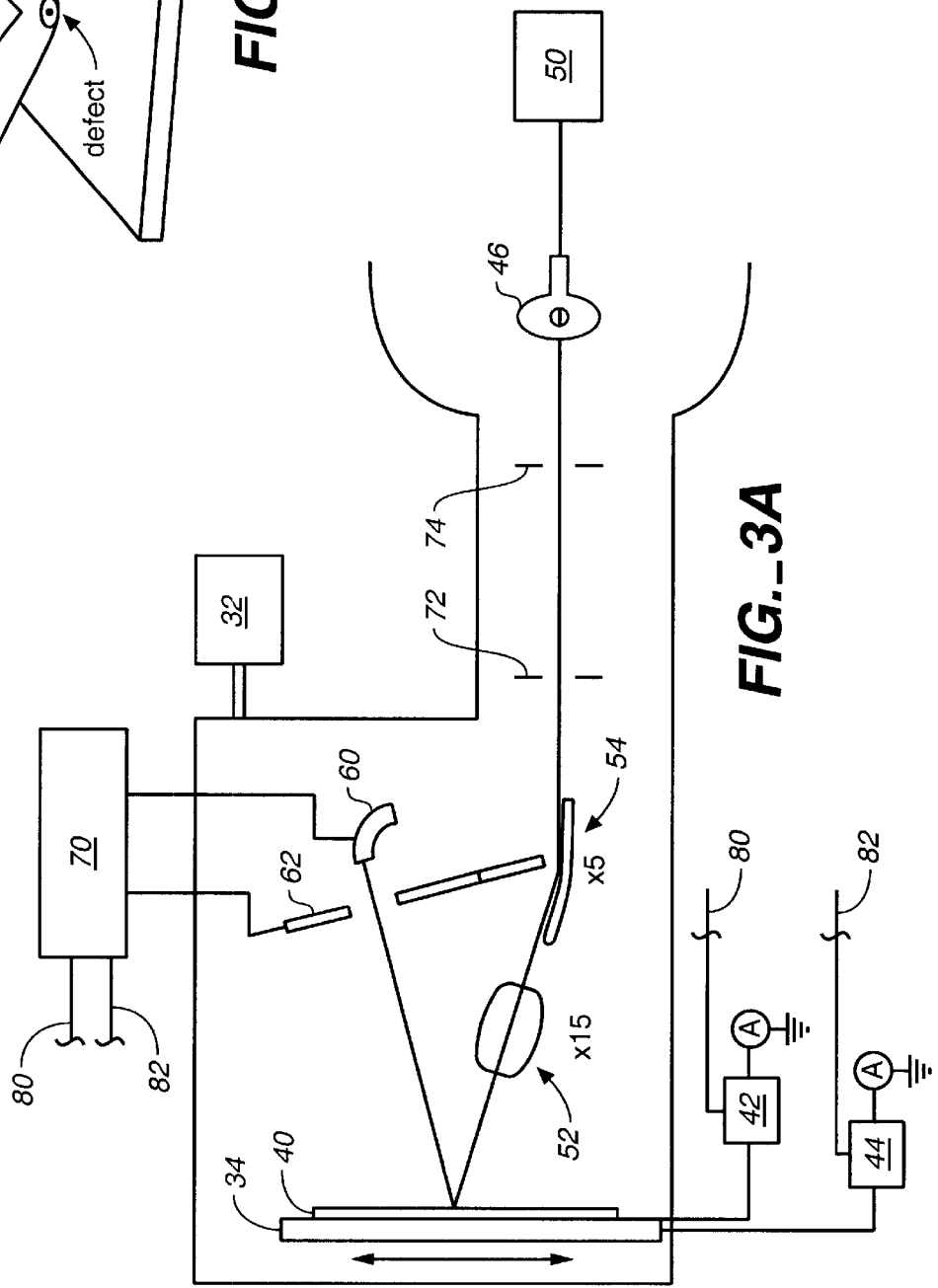
FIG._3A
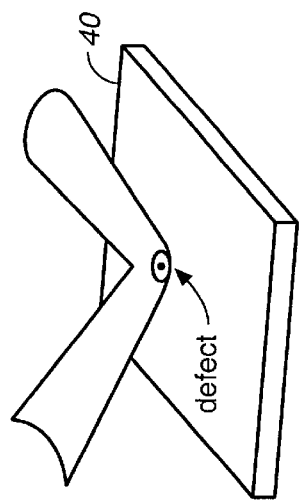
FIG._3B

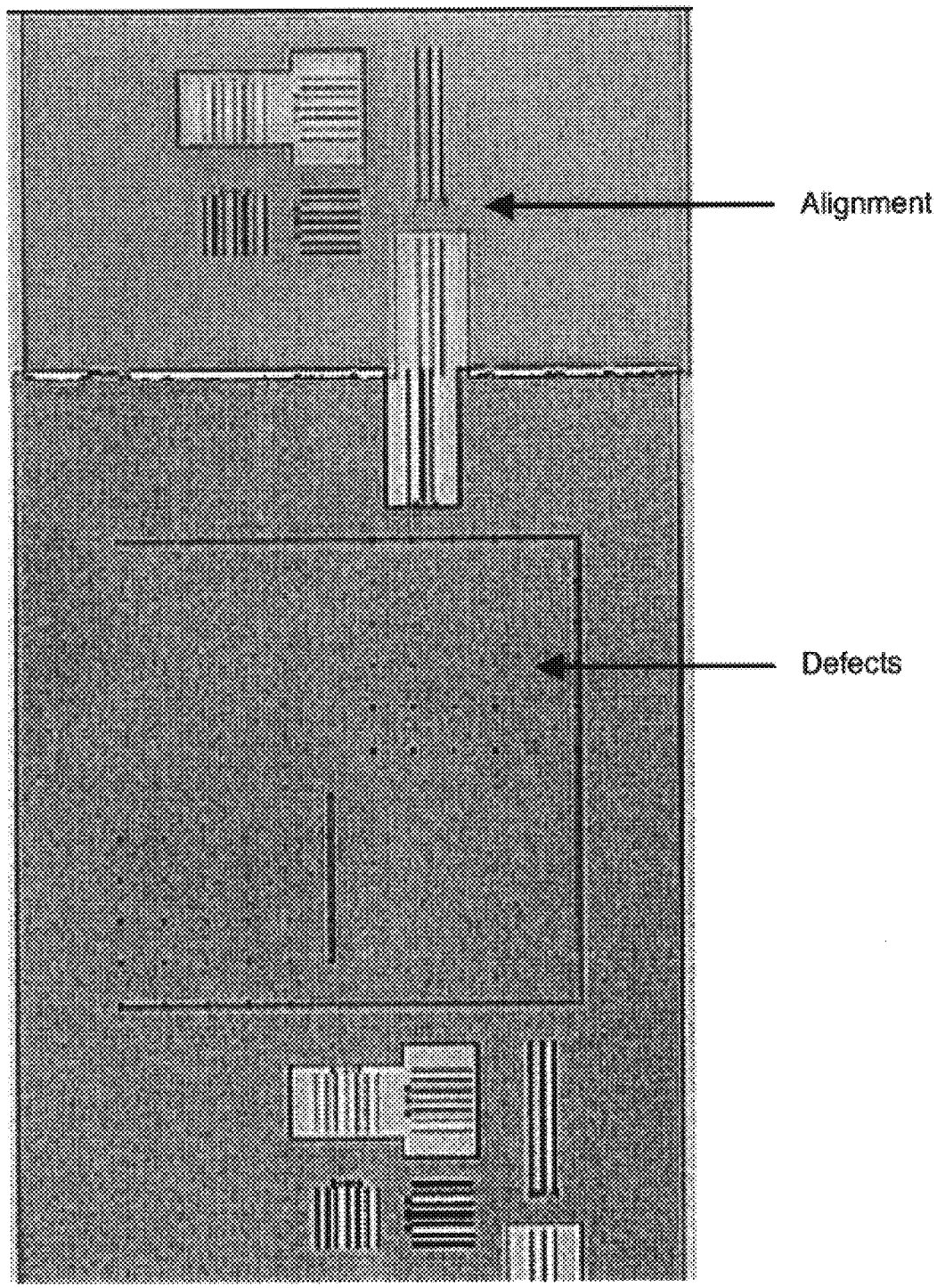
FIG._4

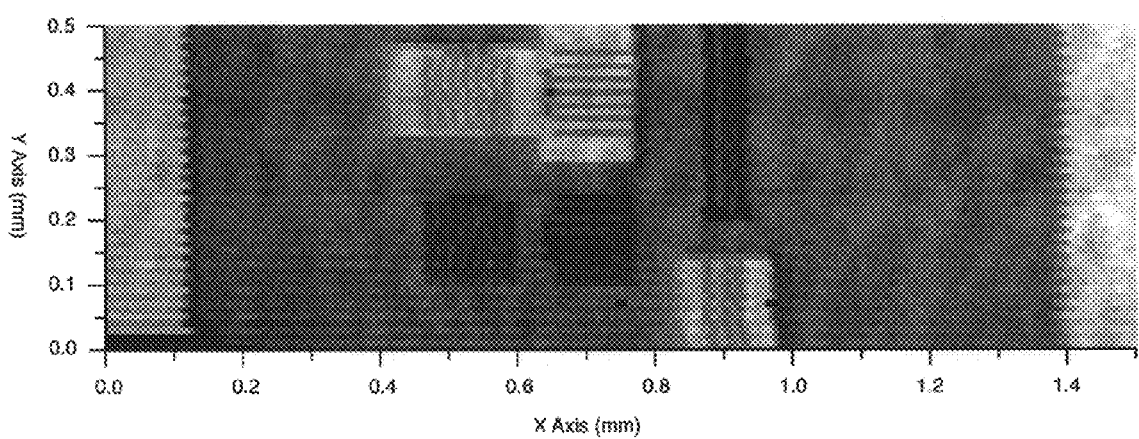
FIG._5

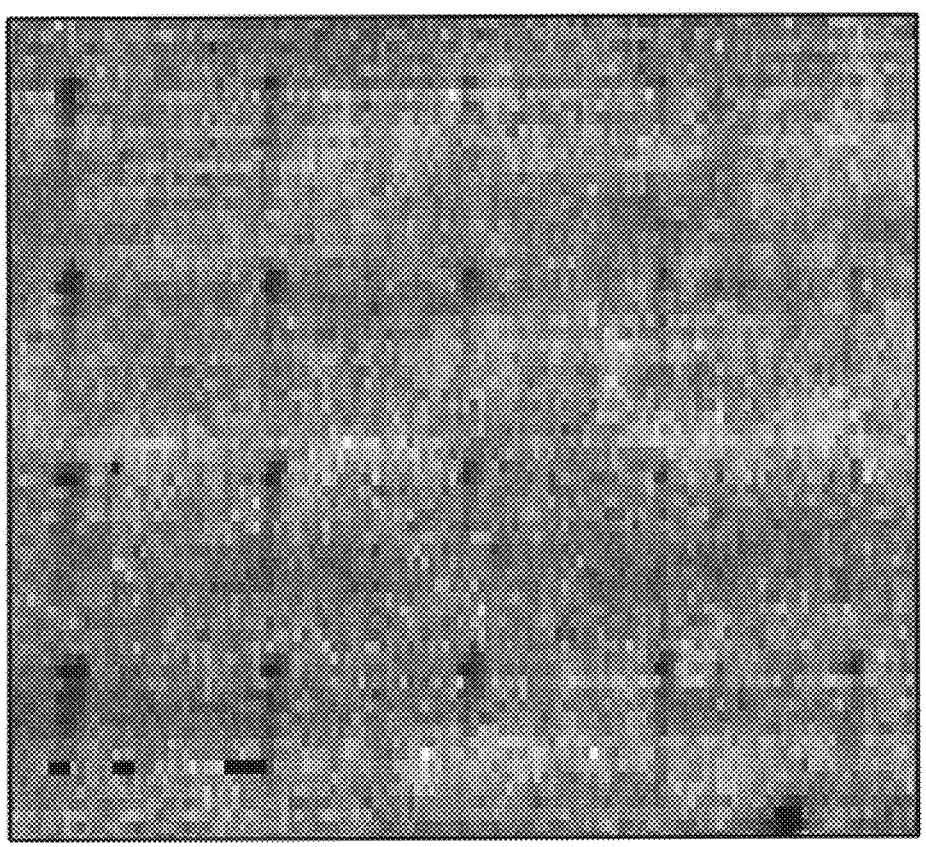
FIG._6
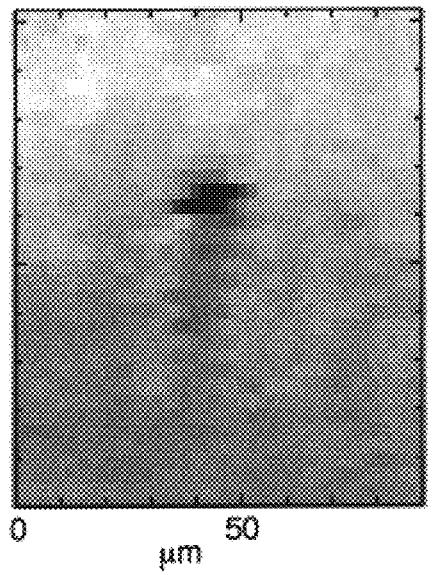
FIG._7

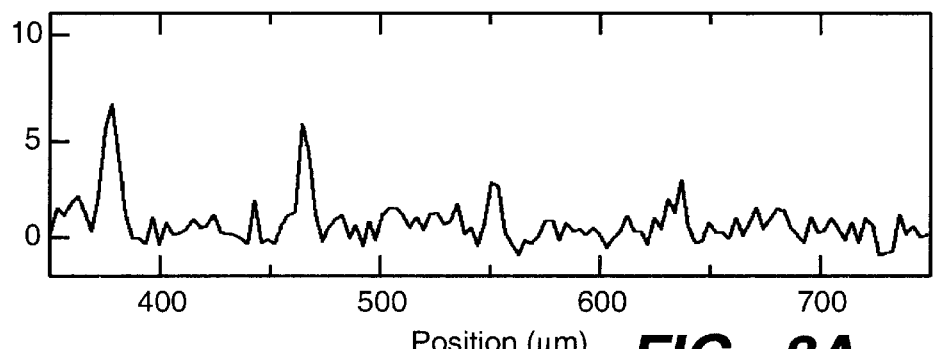
FIG._8A
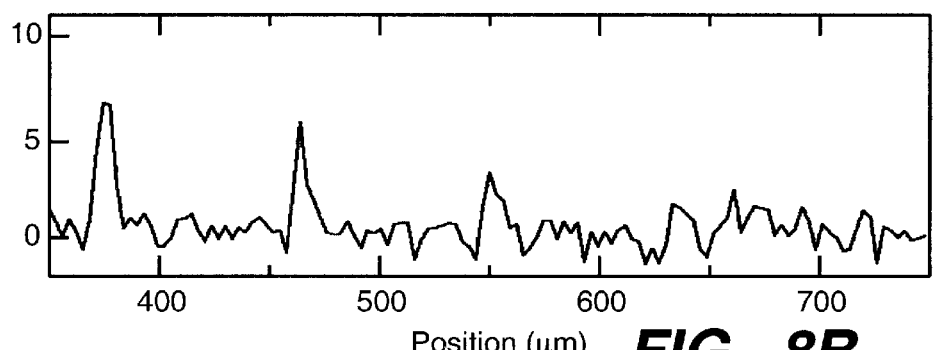
FIG._8B
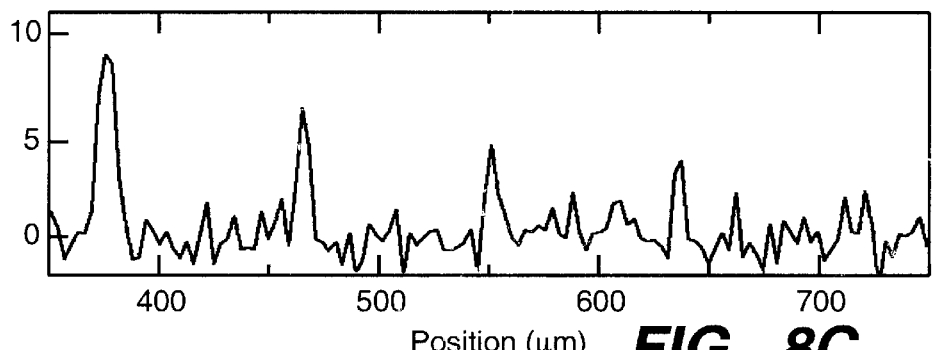
FIG._8C
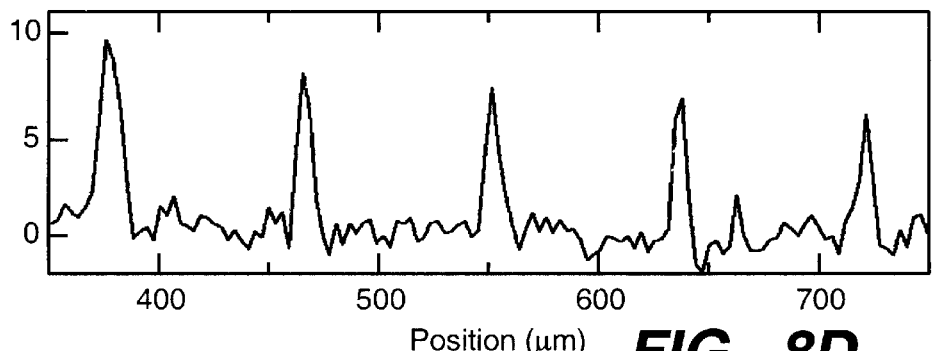
FIG._8D

METHOD AND APPARATUS FOR INSPECTING REFLECTION MASKS FOR DEFECTS

The U.S. Government has certain rights in this invention pursuant to Contract No. DE-AC03-76SF00098 between the United States Department of Energy and the University of California for the operation of the Lawrence Berkeley National Laboratory.

FIELD OF THE INVENTION

This invention relates to an at-wavelength EUVL mask blank inspection system based on scanning of a focused EUV beam onto the mask blank surface and correlating the intensity of the specular reflection and defect scattering to potential defects at and below the surface of the mask blank.

BACKGROUND OF THE INVENTION

Extreme ultraviolet lithography (EUVL) is a promising technology for integrated circuit fabrication for feature sizes less than 0.1 $\mu$m. It is an optical projection lithography scheme using short wavelength radiation with all-reflective optics based on multilayer coatings. An EUVL reticle is also reflective, consisting of a multilayer coated substrate and a patterned absorber layer. In order to insure the integrity of the printed pattern, the reticle has to be free of any critical defect which can occur either on the absorber pattern or on the mask blank itself. While several techniques have been proposed for correcting defects in the absorber overlayer pattern, there is no known repair technology for defects in the multilayer coating. Moreover, the defects in the multilayer coating have been shown to be more detrimental than absorber defects of the same dimension and those defects may be very hard to detect. A recent defect printability study by Lin & Bokor, J. Vac.Soc. and Tech. B 15(6) pp2467 Nov/Dec 1997, showed that a totally opaque defect in the mask blank as small as 40 nm will produce 10% process window reduction for a 0.1 $\mu$m contact hole. The ability to produce and certify mask blanks with low defect density is a critical issue for the economic viability of EUVL technology.

SUMMARY OF THE INVENTION

The present invention is based in part on the recognition that when a focused EUV beam is incident on a defective region of a mask blank, three possible phenomena can occur. The defect will induce an intensity reduction in the specularly reflected beam, scatter incoming photons into an off-specular direction, and change the amplitude and phase of the electric field at the surface which can be monitored through the change in the photoemission current. The magnitude of these changes will depend on the incident beam size, and the nature, extent and size of the defect. Inspection of the mask blank is performed by scanning the mask blank with EUV light focused to a small spot (typically a few microns or less in diameter), while measuring the reflected beam intensity (bright field detection), the scattered beam intensity (dark-field detection) and/or the change in the photoemission current. Defects in the mask will cause changes in the electric field on the surface of the substrate. This can be detected by monitoring changes in the photoemission current.

Accordingly, in one aspect the invention is directed to a method for detecting defects at or below the surface of a mask substrate that includes the steps of:

directing extreme ultraviolet (EUV) radiation, typically having a wavelength of 5–15 nm, on a region of the surface of the mask substrate;

measuring the intensity of the specular reflection and the intensity of the defect scattering from the region; and determining whether defects are present on the mask substrate surface.

In a preferred embodiment, the size and phase of the defects is determined by developing functional relationships between the measured intensities of the specular reflection and the defect scattering and the size of the defect on the region and the phase information for the region.

The feasibility of the at-wavelength mask blank inspection system has been demonstrated. From initial scans on a programmed phase defect mask, a prototype system is shown to be sensitive to phase defects down to 0.5 by 0.8 $\mu$m with a beam size 4×6 $\mu$m. Currently, improvements to the beam spot size are being actively pursued to achieve an EUV beam spot with about 1 $\mu$m diameter.

BRIEF DESCRIPTION OF THE DRAWINGS

FIG. 1 is a schematic diagram of the scattered light components from an EUV beam that is focused on a blank mask;

FIG. 2 illustrates the super position of E-fields;

FIG. 3A is a schematic of the at-wavelength inspection apparatus;

FIG. 3B illustrates the reflection of the EUV beam from the blank mask;

FIG. 4 is a photograph of a programmed defect mask layout showing the resist pattern;

FIG. 5 is a bright field scan through alignment marks with a pixel size of 10×10 $\mu$m;

FIG. 6 is a Gray-scale image of a 2D programmed defect mask with a pixel size of 3×5 $\mu$m;

FIG. 7 is a magnified image of a defect on the leftmost defect of the bottom row of FIG. 6; and FIGS. 8A, 8B, 8C and 8D show line scans for reflectivity reduction along the programmed defects (the vertical axis is %).

DESCRIPTION OF THE PREFERRED EMBODIMENTS

The scanning system of the present invention uses combined bright-field/dark-field measurements to accomplish at-wavelength inspection of blank EUV lithography masks. Although the invention will be described using 13 nm EUV radiation, it is understood that the invention can employ EUV radiation in general and typically the EUV will have a wavelength of about 5 to 15 nm.

As illustrated in FIG. 1, a 13 nm EUV beam is focused into a small spot (about 1 $\mu$m) on the surface of an EUVL blank mask 10. Both the scattered light in the off-specular direction (dark-field) 12 and the reflected light in the specular direction (bright-field) 14 can be used as indications of possible defects on the mask 10. The components of the scattered light further comprise wings on the specular beam (flare) 16 and diffuse scatter 18. A detector 20 is strategically positioned as shown. The incident beam of the EUV radiation is focused on surface regions typically having a size (e.g., diameter) of about 0.1 to 10 microns and preferably about 0.1 to 1 micron.

The following discusses the theoretical basis for the scanning system; it is understood that the invention is not limited to any particular theory.

In the case of a totally opaque defect, the scattered intensity scales with the area. If the incident spot is 1 $\mu$m in diameter, and the defect under inspection is 0.1 $\mu$m in diameter, then the total scattered light power is $\frac{1}{100}$ of the total incident light power. The scattered light is diffracted into a solid angle that is 100 times larger, so the scattered intensity is $10^{-4}$ of the specular intensity. This means that the form of the fall-off of specular intensity outside the specular cone is a critical issue. This fall-off must be made sufficiently steep so that it does not become the dominant source of background.

Under this condition, the background in the dark-field signal is dominated by the diffuse background scatter due to the imperfect nature of the multilayer coating. Data on representative Mo/Si multilayer coatings show that the background scatter per steradian is 4% of the incident beam. The total background collected in a certain solid angle is therefore $$N = 0.04 I_0 \pi \phi^2 \tag{1}$$

Here, $I_0$ is the incident intensity, and $\pi\phi^2$ is the approximate collection solid angle for small $\phi$, where $\phi$ is the collection half angle of the dark-field detector.

Assuming that the background scatter intensity is constant with respect to time, the noise in the dark-field would just be the shot noise fluctuation of this constant background scatter, which is dependent on the measurement time. In the case of a complete opaque defect, in order to have a signal to background ratio of larger than one, then $$R I_0 \frac{A_d}{A} t > (0.04 I_0 \pi \phi^2 t)^{1/2}$$

where R is the reflectivity of the multilayer mirror, $A_d$ is the area of the defect, and A is the incident spot area. It was assumed that $\phi$ is chosen large enough to capture the diffraction angle of the smallest defect to be detected. This sets a lower limit on d, given by $$R \pi d^2 > A (0.04 \pi \phi^2)^{1/2} (I_0 \cdot t)^{-1/2}$$

$$d^4 > \frac{0.04 A^2 \phi^2}{\pi R^2 I_0 \cdot t} \tag{2}$$

The limitations on partially opaque defects and phase defects can be found in similar fashions.

$$d^4 > \frac{0.04 A^2 \phi^2}{\pi R^2 (1-a)^2 I_0 \cdot t} \tag{3}$$

$$d^4 > \frac{0.04 A^2 \phi^2}{\pi R^2 2(1-\cos\theta) I_0 \cdot t} \tag{4}$$

It is evident that higher incident intensity and longer dwell time at each spot would enable us to capture smaller defects.

The signal being measured in the bright-field is the intensity of the specular cone. However, the information that is needed is the reduction of the bright-field signal due to the presence of defects, which could be on the order of 1%, since the smallest defect to be captured is typically about 1% of the incident spot area. The noise in the bright-field signal can be divided into two types. One is the inherent shot noise. The other is the fluctuation in the beam, resulting from any instability in the incident source. These noise sources impose a lower limit on the defect-induced reduction that can be identified. This translates to a minimum defect size that this system can detect. It is believed that the actual beam fluctuation will be on the order of a fraction of 1%. This is smaller than the rough estimate of the bright-field signal reduction caused by defects.

Combining the Bright and Dark Fields

In the bright-field scheme defects smaller than a certain size cannot be detected as discussed above. In the dark-field scheme large defects cannot be detected as the scatter angle of the defects gets too close to the reflected beam itself. The optimum solution is to have both signals measured at the same time when the mask is being scanned. This can be accomplished using a microchannel plate (MCP) with a hole in the middle as the dark-field detector, allowing the reflected beam to go through unobstructed, which can then be picked up by a channeltron detector. MCP detectors with a suitable center hole are commercially available. The choice of channeltron enables one to detect high intensity at the shot-noise-limit. Since the shot noise in both the bright-field and dark-field could be the deciding factor when minimizing the dwell time, higher intensity is more desirable. A high dynamic range channeltron can handle up to $10^9$ counts per second when operated in analog mode, and still be dominated by shot noise.

In a preferred embodiment, the MCP that will be used has a 40 mm working diameter and a 6.4 mm center hole. This particular choice of MCP configuration for the following calculations is based on the availability of a synchrotron source of EUV radiation (referred to herein as the "Beam line") at the advanced light source (ALS) at Lawrence Berkeley National Laboratory. The Beam Line will have a maximum horizontal divergence of 27.75 mrad and a vertical divergence of 7.5 mrad after the Kirkpatrick Baez (KB) focusing mirrors. In order to pass the beam through the 6.4 mm center hole, the MCP needs to be placed within 23 cm of the mask. A distance of 17 cm was selected to account for possible beam divergence degradation caused by the KB performance. The MCP collects a half angle of 0.117 rad, so the background scatter collected is about 0.2% of the incident beam according to equation (1).

To capture defects that produce a 5% reduction in the reflected beam, at least 400 counts in every measurement are needed. The Beam line can deliver approximately $4 \times 10^8$ photons per second (pps) into a 1 $\mu$m by 1 $\mu$m spot. The reflected beam flux is $3 \times 10^8$ pps after the reflection of the multilayer sample. Assuming a quantum efficiency of 7% for an uncoated channeltron (could be up to 20% for $MgF_2$ coated channeltron), a 20 μsec dwell time per 1 μm spot to obtain the 400 counts is required. By increasing the dwell time, correspondingly smaller defects can be detected.

If the incident beam has $4 \times 10^8$ pps as stated above, and the wings on the specular cone (which is called the flare 16 in FIG. 1), are negligible compared to the diffuse background scattering, then the background noise is $8 \times 10^5$ pps according to equation (1). In 20 μsec (same as in brightfield), the background is about 16 photons, which results in about 1 detected count. Assuming that this background scatter is constant, then the noise is the shot noise fluctuation of this background scatter in each measurement. In this case it is about 1 count, so we should be able to capture defects that result in more than 1 count of dark-field scatter per 20 μsec.

With a dwell time of 20 μsec on a 1 μm spot, it will take 33 minutes to scan a 1 cm by 1 cm area. To detect a 1% fluctuation in the reflected beam with the same signal to noise ratio, the dwell needs to be increased time by 25 times. The scanning speed of this system is limited by the source intensity with the current parameters of the Beam line. Clearly, it is preferred to decrease the scan time significantly in order to be able to scan a full 6 in. or even 8 in. mask blank. With a $MgF_2$ coating, a factor of 3 improvement is possible without affecting other system parameters. It is also possible to re-optimize the Beam line and focusing optics to further increase the flux into the same 1 μm spot size. It is expected the improved KB systems may also allow for the possibility of sub-micron spot size.

The key unknowns in the experiment are the main beam profile (flare) and flux, the capacity of the bright-field detector, the fluctuation of the main beam, and the performance of the KB optics. The reflected beam profile will affect the dark-field performance if the flare makes a significant contribution to the dark-field background level. The fluctuation in the main beam would limit the performance of the bright-field as mentioned before. This would affect the detection capability of large defects with small reflectivity reduction. The performance of the KB optics determines the size of the spot. If the area of the spot increases, the flux density decreases. In both the bright-field and dark-field, the signal scales with the flux density times the dwell time. In the bright-field, the noise is the shot noise of the reflected beam. In the dark-field, the noise is the shot noise of the background scatter. Both scale with the square root of the multiple of the total flux and the dwell time. Therefore, in order to maintain the same signal to noise level, the dwell time has to scale with the $4^{th}$ power of the linear spot size, and so the total scan time scales with the square of the linear spot size, or the spot area. However, the scanning speed scales with the inverse of the spot area. So increased spot size will make the mechanical design easier at the expense of detection speed.

Based upon the considerations discussed here, it is estimated that a practical defect scanner should have a flux exceeding $10^9$ photons/sec delivered to a <1 μm focal spot on the mask. It will be important to minimize the flare of the focused beam by using high quality (smooth) mirrors for the KB optics and apertures to baffle out residual flare.

Although a prototype scanner fielded on the Beam line will not reach these performance specifications, as demonstrated herein the scanner does come sufficiently close to permit proof of principle experiments that can be compared to the calculations presented here. The productivity of this scanner will be sufficient to provide meaningful data on defect counts on EUV mask blanks, as well as on programmed defect masks.

Experimental

A schematic layout of a prototype at-wavelength inspection system is shown in FIG. 3A. The inspection system is enclosed in a vacuum chamber 30 that is connected to vacuum pump 32. During operation, the vacuum chamber is typically maintained at a pressure level between $10^{-6}$ torr to $10^{-7}$ torr and preferably at about $10^{-7}$ torr. The vacuum chamber is mounted to a synchrotron source, i.e., Beam line. The sample mask substrate 40 is kinematically mounted on an X-Y linear stage 34 with 150 mm travel in either direction allowing a scan of a full 6 inch wafer. The stage is driven by dc-servo motors 42 and 44 (one motor per axis) with position accuracy preferably better than 1 μm. Motors 42 and 44 are connected to control lines 80 and 82, respectively. The small spot or region of EUV light is achieved by demagnifying an illuminated pinhole aperture 46 with a glancing incidence optical system having two mirrors 52 and 54 arranged in the Kirkpatrick-Baez (K-B) configuration. To eliminate spherical aberration and achieve optimum on-axis image quality each mirror has the form of an elliptic cylinder. This figure was achieved by bending strip mirrors with unequal end couples, as described in J. H. Underwood, Space. Sci. Inst. 3, 259, 1977. The side profiles of mirrors were profiled to obtain a longitudinal variation of the cross-sectional moment of inertia, and hence accurate bending into the required ellipse.

The focusing system is designed to demagnify a 25 μm pinhole placed at the object plane of the K-B optics. With a demaginification factor of 15 in the horizontal plane and 5 in the vertical plane, the optics should thus provide 1.7×5 μm spot on the mask blank located at the image plane of the K-B system. The approximate size and shape of the focused beam is monitored by observing, with a microscope, the fluorescence of a YAG crystal situated at the sample plane. Its size in orthogonal directions, measured using a knife edge scan, was conservatively estimated to be 4×6 μm FWHM (full width at half maximum). Several factors contribute to make the observed spot size larger than the geometrical prediction. These include: imperfections of the mirrors and bending mechanism, alignment errors and 1 μm resolution of the stage motion.

As shown in FIG. 3B, the focused beam is incident on the sample 40 with an angle of 9 degrees off normal and the reflected beam and the scattered photons are detected by the detector assembly which is located 15 cm away from the sample. The detector assembly includes a channeltron electron multiplier 60 for the bright field measurement and microchannel plate 62 for the dark field detection. The microchannel plate has a hole at the center in order for the specularly reflected beam to be detected by the channeltron detector situated behind the microchannel plate. The channeltron detector can deliver up to $10^7$ gain at 2700 V bias voltage with a good linearity and has been measured to deliver shot-noise limited performance even in an analog current output mode. The output of the channeltron was read through a current amplifier (not shown). For a higher-rate data acquisition which is essential for a high-throughput inspection system, the data was taken while continuously moving the motors and polling the motor's position instead of taking data while the motor is stationary at a specified position. Data acquisition rates of several kHz are achievable with this scheme. The system is controlled through a motor control unit and analog-to-digital converter module in a VXI crate with a computer all shown collectively as element 70.

As an initial proof-of-principle experiment, a test mask blank with programmed defects of known size and location was scanned to quantify the performance of the inspection system. This programmed defect mask was fabricated on a 6 inch silicon wafer by etching the substrate except for a predefined region and mask alignment marks. The resist layout is shown in FIG. 4. The etch depth surrounding the alignment marks is 100 nm while the region surrounding the programmed defects was etched 25 nm deep. After the substrate etch step, the Si/Mo multilayer was deposited by the ion beam sputtering deposition developed for low defect density Si/Mo coating. Multilayer coatings are known in the art. See, e.g., Vernon et al., OSA TOPS on Extreme Ultraviolet Lithography, Vol. 4, G. D. Kubiak and D. Kania, eds., 1996, Optical Soc. of America. Therefore, the Si/Mo multilayer coating over the unetched region is 25 nm high compared to the surrounding region and acts as a phase defect with a phase error of $7.7\pi$. There is a 5 row and 5 column array of rectangular programmed phase defects. The size of the defects varies from $8 \times 1.5$ $\mu$m to $0.2 \times 0.2$ $\mu$m as shown in Table 1. The spacing between defects is 80 $\mu$m in either direction. The scanning wavelength is 13.2 nm with an estimated fractional bandwidth of $1/3000$. Only the bright field signal was collected for these experiments.

TABLE 1

Programmed defect size (Units: $\mu$m)

|  | Column 1 | Column 2 | Column 3 | Column 4 | Column 5 |
| --- | --- | --- | --- | --- | --- |
| Row 5 | 8 × 0.2 | 4 × 0.2 | 2 × 0.2 | 0.5 × 0.2 | 0.2 × 0.2 |
| Row 4 | 8 × 0.5 | 4 × 0.5 | 2 × 0.5 | 0.8 × 0.5 | 0.5 × 0.5 |
| Row 3 | 8 × 0.8 | 4 × 0.8 | 2 × 0.8 | 1.1 × 0.8 | 0.8 × 0.8 |
| Row 2 | 8 × 1.1 | 4 × 1.1 | 2 × 1.1 | 1.5 × 1.1 | 1.1 × 1.1 |
| Row 1 | 8 × 1.5 | 4 × 1.5 | 3 × 1.5 | 2.0 × 1.5 | 1.5 × 1.5 |

FIG. 5 is a gray-scale image of a two-dimensional bright field scan of the alignment marks with the pixel size of $10 \times 10$ $\mu$m. The reflectivity of the bright region was separately measured to be 61.8%. The dark region surrounding the alignment marks shows approximately 30% lower reflectivity relative to the bright region. This reduction in reflectivity occurs uniformly over the bandwidth of the given multilayer. Since these two regions have different etch depth as described previously, the reduction in reflectivity is likely due to the roughening of the substrate during the etch step, thus increasing scattering. The features that appear as lines are actually series of squares of size ranging from 3 to 4 $\mu$m. The spacing between the squares varies from 6 to 8 $\mu$m. Individual squares are not resolved in these initial experiments due to the finite pixel size but each linear chain of squares which are 20 $\mu$m apart from each other is clearly resolved. The wavy appearance of the line was traced to a systematic error in the motor drive.

FIG. 6 shows a scan over the region containing programmed defects. The pixel size was 3 by 5 $\mu$m and the dwell time per pixel was 50 msec with the total scan time was 6 minutes. The regularly spaced dark dots are programmed defects showing reduced reflectivity in the bright field. In the bottom row, five programmed defects are clearly observed. The smallest detected defect has the dimension of 0.5 by 0.8 $\mu$m as can be seen in the line scan through the top row in FIG. 8A. The 0.5 by 0.8 $\mu$m phase defect shows a reflectivity reduction greater than the background fluctuation which was approximately 1%. This background fluctuation is mainly due to the shot noise fluctuation according to the estimated number of detected photons per pixel. There are vertical streaks observed around the programmed defect region and these are due to the tail of the focused EUV spot which arises from residual spherical aberration of the K-B optics. A magnified image of the leftmost programmed defect in the bottom row, as shown in FIG. 7, reveals the orientation and magnitude of the defect. It was observed that several "real" defects were observed in the scanned image of the test mask in addition to the programmed defects. One of them is shown at the bottom of the FIG. 6. These "real" defects are quite likely to be a particulate contamination incurred during handling of the mask blank in a non-clean environment. A clean and low particulate environment is essential for counting defects on an EUVL mask blank and providing a meaningful number for the defect density. Efforts such as improving the mask handling protocol and creating a clean mini-environment to reduce the particulate contamination are currently underway. It is noted that no obvious sign of carbon contamination was found for the duration of the scan reported even with focused radiation on the test mask blank.

FIGS. 8A, 8B, 8C and 8D show the corresponding reflectivity reduction along the lines containing the defects. The leftmost peak in each figure (or row) has wider width than the rest in the same figure. This is due to the fact that the horizontal dimension of the leftmost defect is greater than that of the focused beam. Despite a factor of four difference in area between the leftmost defect and the right most defect of the bottom row, the peak reflectivity reduction does not scale accordingly. This is typical of phase defects for which the reflectivity reduction depends not only on the size of the defect but also on the geometry of the defect with respect to the beam size in a rather complicated fashion.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A method fob detecting defects at or below the surface of a mask substrate that comprises the steps of:

directing extreme ultraviolet (EUV) radiation on a region of the surface of the mask substrate;

measuring the intensity of the specular reflection and the intensity of the defect scattering from the region;

determining the presence of defects on the mask substrate surface;

generating first signals that are proportional to the measured intensity of the specular refelection and second signals that are proportional to the measured intensity of te defect scattering; and combining the first and second signals to determine both the size of the defect on the region and the phase information for the region.

2. The method of claim 1 further comprising the step of scanning the mask substrate surface.

3. The method of claim 1 further comprising the step of scanning the EUV radiation across the substrate surface.

4. The method of claim 1 wherein the step of directing EUV radiation comprises directing EUV radiation from a synchrotron to the region.

5. The method of claim 1 wherein EUV radiation has a wavelength of about 13 nm.

6. The method of claim 1 wherein the step of directing the EUV radiation directs an incident beam of the EUV radiation on a region of the surface wherein the region has a size of 0.1 to 10 microns.

7. The method of claim 1 further comprising monitoring photoemission current from the surface of the mask to determine changes in the electric field at the surface of the mask substrate.

8. An apparatus for detecting surface defects at or below the surface of a mask substrate that comprises:

a source of extreme ultraviolet (EUV) radiation;

optical system for directing and focusing a beam of the EUV radiation from the source onto a region on the surface of the mask substrate;

means for measuring the specular reflection and defect scattering from the region;

means for determining the present of defects on the mask substrate surface; and means for generating first signals that are proportional to the measured intensity of the specular reflection and second signals that are proportional to the measured intensity of the defect scattering, and wherein the determining means include means for combining the first and second signals to determine both size and phase of the defects.

9. The apparatus of claim 8 comprising means for scanning the mask substrate surface to direct the EUV radiation to a plurality of regions on the mask substrate surface.

10. The apparatus of claim 8 wherein EUV radiation has a wavelength of about 13 nm.

11. The apparatus of claim 8 wherein the optical system directs an incident beam of the EUV radiation on a region of the surface wherein the region has a size of 0.1 to 10 micron.

12. The apparatus of claim 8 further comprising means for measuring changes in photoemission current from the surface of the mask to determine changes in electric field at the surface of the mask surface.

* * * * *